United States Patent [19]
Lewis et al.

[11] Patent Number: 6,122,980
[45] Date of Patent: Sep. 26, 2000

[54] MIXING SYSTEM

[75] Inventors: Gary W. Lewis, Foothill Ranch, Calif.;
William M. Silvis, Ann Arbor, Mich.

[73] Assignee: Horiba Instruments, Inc., Irvine, Calif.

[21] Appl. No.: 09/105,350

[22] Filed: Jun. 26, 1998

[51] Int. Cl.[7] .............................. G01N 1/20; G01N 1/38
[52] U.S. Cl. .................................. 73/863.43; 73/863.12; 73/863.61; 73/863.81; 137/896
[58] Field of Search ........................ 73/863.43, 863.12, 73/863.61, 863.11, 863.23, 863.81; 137/896

[56] References Cited

U.S. PATENT DOCUMENTS

| | | | |
|---|---|---|---|
| 3,744,215 | 7/1973 | Barnes, Jr. | 95/271 |
| 4,164,960 | 8/1979 | Howard | 137/604 |
| 4,312,480 | 1/1982 | Miller | 239/127.3 |
| 4,330,510 | 5/1982 | Schauer et al. | 423/210 |
| 4,387,914 | 6/1983 | Paulson et al. | 285/119 |
| 4,662,174 | 5/1987 | Toulmay | 60/264 |
| 4,823,591 | 4/1989 | Lewis . | |
| 5,060,984 | 10/1991 | Hess | 137/599 X |
| 5,077,016 | 12/1991 | Layng et al. | 137/846 X |
| 5,821,435 | 10/1998 | Kojima | 73/863.01 |

FOREIGN PATENT DOCUMENTS

| | | |
|---|---|---|
| 2205712 | 8/1973 | Germany . |
| 3433 090 A1 | 3/1986 | Germany . |
| 196 31 922 A1 | 2/1997 | Germany . |
| 74407 | 4/1984 | Japan . |
| 02223624 | 6/1990 | Japan . |

OTHER PUBLICATIONS

Dialog(R) File 351: Derwent WPI (c) 2000 Derwent Info Ltd. WPI ACC No: 86–082409/* 198613* Abstract of DE 3433090 A, Mar. 1986.
"Draught Increasing Arrangement for Tile Stove Chimneys Suction has Branch out of Chimney Coupled to Mixer Tube by Elbow Connection", Inventor H. Struss.

*Primary Examiner*—Thomas P. Noland
*Attorney, Agent, or Firm*—Brooks & Kushman P.C.

[57] ABSTRACT

A mixing system includes a dilution inlet, an elbow duct, and a gaseous inlet in flow communication with the elbow duct along the elbow duct outer turning radius. The elbow duct has a first end in flow communication with the dilution inlet, and a second end outlet for connecting to external equipment, such as a sampling system.

19 Claims, 3 Drawing Sheets

MIXING SYSTEM

TECHNICAL FIELD

The present invention relates to measurement and dilution techniques for analysis of gaseous constituents.

BACKGROUND ART

A gas diluting and testing apparatus is used to analyze, among other things, vehicular exhaust. The apparatus uses a mixing tee to dilute the exhaust gases so that the moisture content of the gases is sufficiently reduced in order to minimize errors due to condensation. Existing mixing tees have a dilution inlet for receiving a dilution gas, a gaseous inlet for receiving the exhaust gases, and an outlet for connecting to external equipment, such as a sampling system.

A primary concern in attaching any equipment to a vehicle exhaust pipe is to avoid any excess pressure or vacuum on the vehicle exhaust pipe. Current standards range from +/−1 in $H_2O$ (0.25 kPa) to +/−5 in $H_2O$ (1.25 kPa), depending on the testing program.

A typical flow rate at the mixing tee outlet for some testing programs is about 300–350 $ft^3$/min (8.5–10 $m^3$/min). However, lower fuel economy vehicles and methanol fuel vehicles require a higher dilution flow rate for accurate testing. As such, the testing of these vehicles may require as much as 700–800 $ft^3$/min (20–23 $m^3$/min) flow rate at the mixing tee outlet. With existing mixing tees, increased flow rates at the mixing tee outlet result in increased vacuum at the vehicle exhaust pipe. At these increased flow rates, or at even higher flow rates, it becomes more difficult to stay within specification, particularly in more demanding testing programs which require the +/−1 in $H_2O$ (0.25 kPa) specification.

Also, many testing programs require that the dilution flow rate be monitored during testing. Monitoring the dilution flow rate and the mixing tee outlet flow rate allows calculation of the exhaust flow rate. One way to measure dilution flow rate is with a subsonic venturi. The venturi is located at the dilution inlet. However, due to flow dynamics of the subsonic venturi (and of other flow meters as well), there is a pressure loss between the inlet and the outlet of the venturi. This pressure loss adds to the overall pressure loss between the dilution inlet which is normally at ambient pressure, and the vehicle's exhaust pipe. Again, increased vacuum at the vehicle exhaust pipe may become a problem when testing at higher mixing tee outlet flow rates due to additional pressure losses at the venturi.

Some existing systems use a blower for pressure gain after the dilution inlet venturi to reduce the overall pressure drop, and hopefully keep the exhaust pipe pressure within specification. An example of a mixing tee having an actively controlled blower is described in U.S. Pat. No. 4,823,591 issued to Lewis and assigned to the assignee of the present invention, the disclosure of which is hereby incorporated by reference in its entirety.

Although the above described systems have been used in many applications which have been commercially successful, stricter specifications and higher flow rate demands may become difficult to meet with such systems. Further, systems using active blower control in order to meet specifications are costly; and, tuning such systems may be complicated.

DISCLOSURE OF INVENTION

It is, therefore, an object of the present invention to provide a low-loss mixing system.

In carrying out the above objects and other objects and features of the present invention, a mixing system for diluting gases is provided. The mixing system comprises a dilution inlet, an elbow duct, and a gaseous inlet. The elbow duct has a first end in flow communication with the dilution inlet. A second end outlet of the elbow duct connects to external equipment such as a sampling system. The elbow duct defines an inner turning radius and an outer turning radius. The gaseous inlet receives the gases, which may be exhaust from a vehicle. The gaseous inlet is in flow communication with the elbow duct along the elbow duct outer turning radius.

The flow dynamics of the elbow duct provide a pressure gain along the outer turning radius. This pressure differential across the diameter of the elbow duct is utilized by connecting the gaseous inlet along the outer turning radius of the elbow duct.

Preferably, a flow meter has an inlet in flow communication with the dilution inlet, and has an outlet in flow communication with the elbow duct first end. Further, the flow meter inlet preferably defines a narrowing portion, and the meter outlet preferably defines an exit cone with an exit cone angle between about 5 degrees and about 15 degrees.

In a preferred embodiment, the elbow duct has an average turning radius to diameter ratio between about 0.5 and about 2.5. Further, the elbow preferably bends between about 45 degrees and about 180 degrees. Further, in a preferred embodiment, filters and a heater are located at the dilution inlet for filtering and heating the dilution gas which is usually air at ambient pressure.

Further, in carrying out the present invention, a mixing system comprises a dilution inlet, an elbow duct, and a gaseous inlet in flow communication with the elbow duct along the elbow duct outer turning radius. The mixing system further comprises a sampling system connected to the elbow duct second end outlet.

Still further, in carrying out the present invention, a mixing system comprises a dilution inlet, an elbow duct, and a gaseous inlet. The elbow duct has a first end in flow communication with the dilution inlet, and a second end outlet for connecting to external equipment. The gaseous inlet is in flow communication with the elbow duct along an outer portion of the elbow duct to take advantage of the pressure gain along the outer portion of the elbow duct.

The advantages associated with embodiments of the present invention are numerous. For example, embodiments of the present invention reduce the resultant vacuum on the vehicle exhaust pipe caused by increased mixing system outlet flow rates. Further, embodiments of the present invention are suitable for many applications including vehicular exhaust testing, and may eliminate the requirement of some applications for active blower control.

The above objects and other objects, features, and advantages of the present invention are readily apparent from the following detailed description of the best mode for carrying out the invention when taken in connection with the accompanying drawings.

BEST MODE FOR CARRYING OUT THE INVENTION

Figure 1:
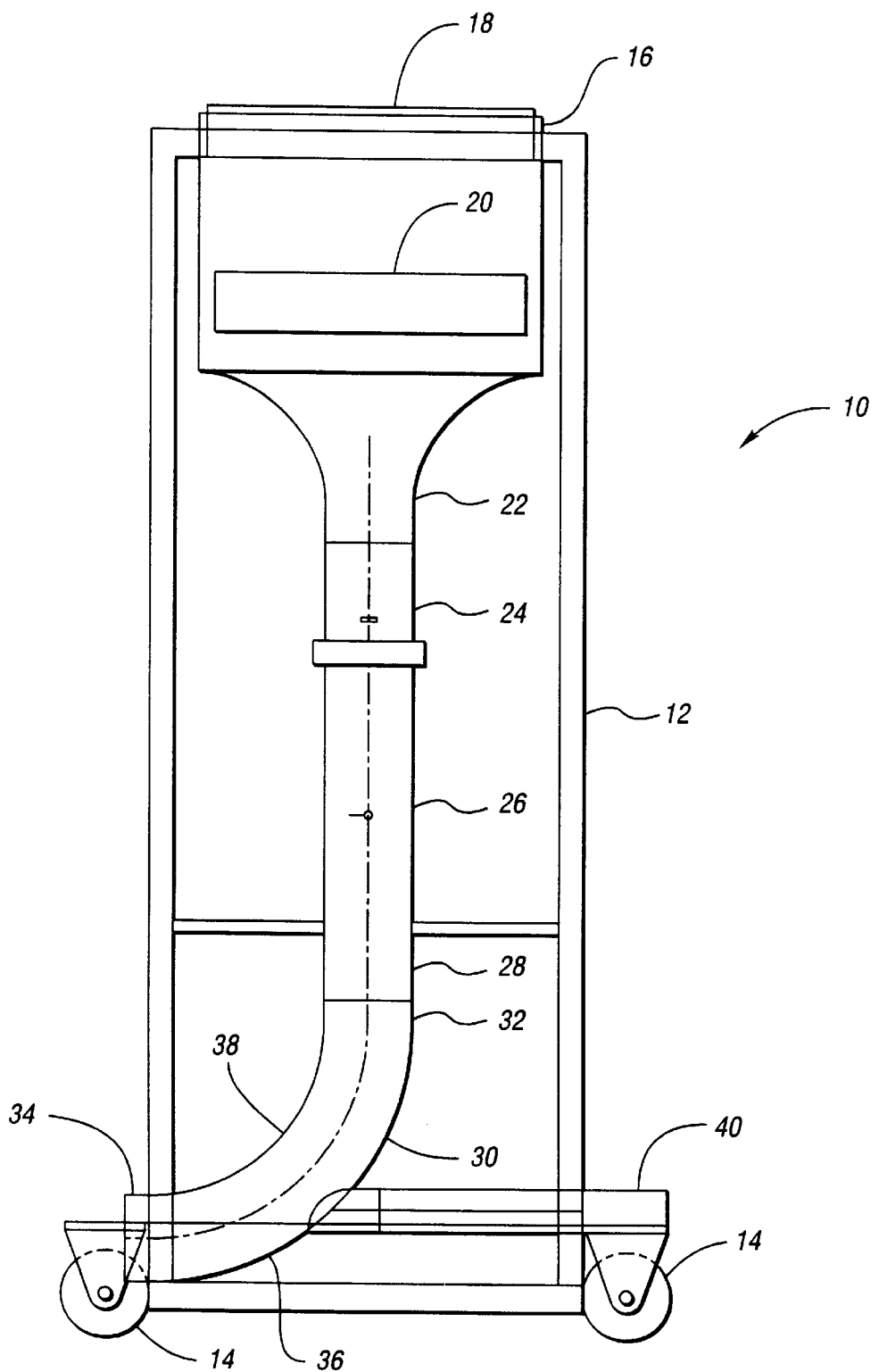
FIG. 1 is a mixing system made in accordance with the present invention.

With reference to FIG. 1, a mixing system of the present invention is generally indicated at 10. Mixing system 10 has a housing 12 supported on wheels 14. Alternatively, system 10 may be suspended from a ceiling or mounted in any other fashion desired. A dilution inlet 16 receives dilution gas which is typically air at ambient pressure, but may be a different gas at a different pressure. Filters 18 at dilution inlet 16 filter dust and dirt from the dilution gas. A heater 20 may be positioned at dilution inlet 16 to heat the dilution gas prior to mixing. Dilution inlet 16 connects to duct 22. Duct 22 connects to a flow meter having an inlet 24. The flow meter has an outlet 26.

The flow meter is configured to indicate the dilution gas flow rate through the flow meter. The end 28 of flow meter outlet 26 connects to an elbow duct 30. Elbow duct 30 has a first end 32 in flow communication with the flow meter, and a second end outlet 34 for connecting to external equipment such as a sampling system.

Elbow duct 30 defines an outer turning radius along outer duct portion 36, and also defines an inner turning radius along inner duct portion 38. Further, elbow duct 30 is preferably bent about 90 degrees. A gaseous inlet 40 receives the gases such as vehicular exhaust gases. The gaseous inlet 40 is in flow communication with elbow duct 30 along the elbow duct outer turning radius. Due to the flow dynamics, elbow duct 30 has intrinsic pressure gain along its outer turning radius. Advantageously, connecting gaseous inlet 40 along the elbow duct outer turning radius reduces gaseous inlet depression or vacuum on the vehicle exhaust pipe.

Figure 2:
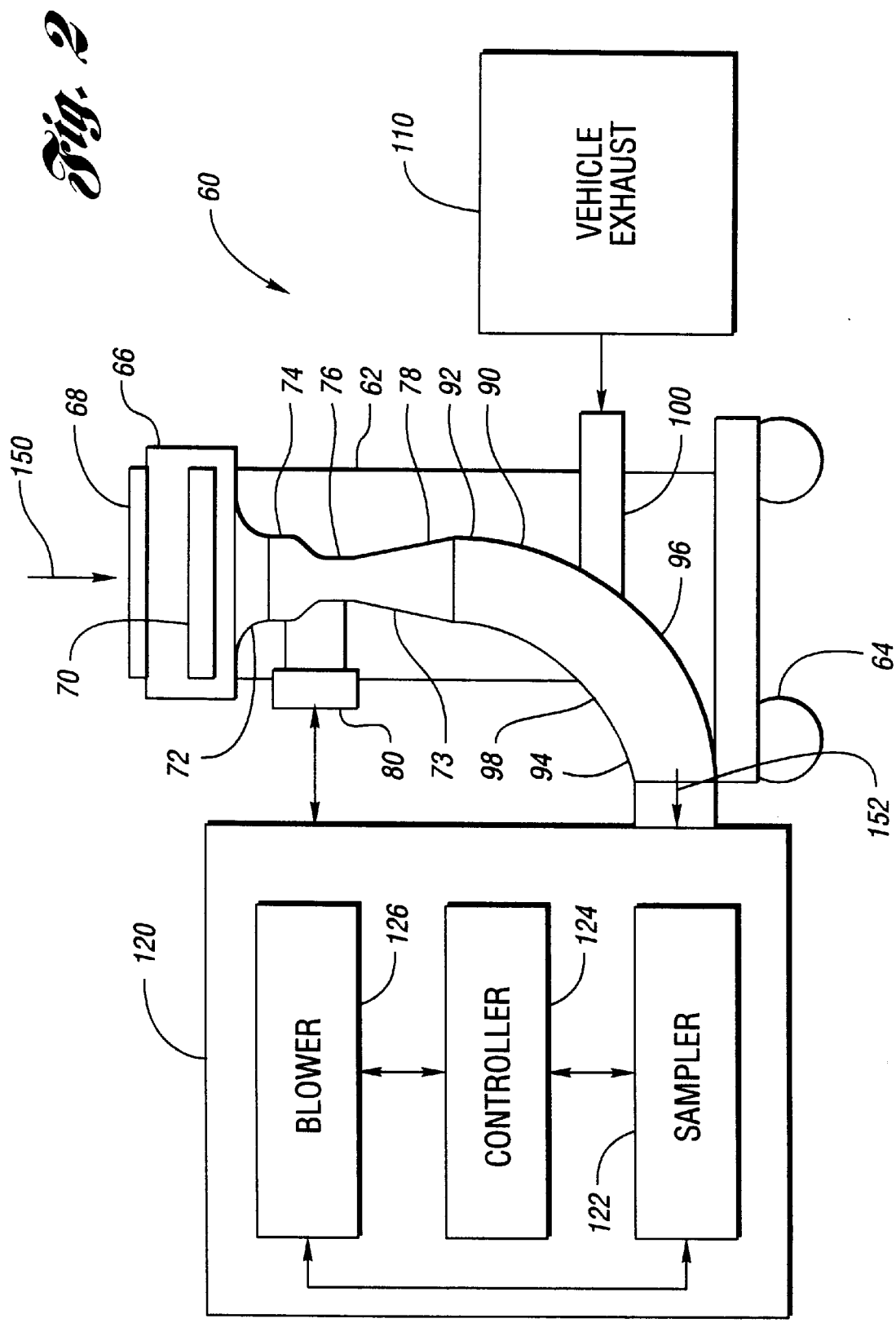
FIG. 2 is a mixing system of the present invention including a sampling system.

With reference to FIG. 2, a mixing system is generally indicated at 60. System 60 has a housing 62, and wheels 64. Dilution inlet 66 preferably contains filters 68 and heater 70. Duct 72 connects inlet 66 to a flow meter 73 having an inlet 74. In addition to inlet 74, flow meter 73 includes a throat 76 and an exit cone 78. Of course, duct 72 and inlet 74 may be combined in a single duct. In a preferred embodiment, the flow meter 73 has an inlet nozzle and a diffuser cone with an exit cone angle between about 5 degrees and about 15 degrees.

A transducer 80 monitors flow meter 73 and produces an output indicative of the flow rate through flow meter 73. In one embodiment, transducer 80 measures pressure at inlet 74 and at throat 76, in addition to measuring temperature at inlet 74. Of course, temperature may alternatively be measured before or after flow meter 73. Further, there are many flow measuring techniques that may be employed in embodiments of the present invention, and the embodiment described above is merely one example.

An elbow duct 90 has a first end 92 in flow communication with flow meter 73. A second end outlet 94 of elbow duct 90 connects to a sampling system. Sampling system 120 may include a variety of components including a sampler 122, a controller 124, which is preferably an embedded microcontroller, and a blower 126. Of course, the system depicted in FIG. 2 is merely one example of a sampling system; other sampling systems are contemplated. For example, some applications may use an air pump instead of a blower.

Elbow duct 90 defines outer and inner turning radii along outer and inner duct portions 96 and 98, respectively. A gaseous inlet 100 receives gases, such as vehicle exhaust 110. In accordance with the present invention, gaseous inlet 100 and elbow duct 90 are arranged such that pressure gain along the outside radius of elbow duct 90 reduces gaseous inlet depression. That is, embodiments of the present invention compensate for resultant increases in vacuum at inlet 100 due to increased flow rates at elbow duct second end outlet 94.

With continuing reference to FIG. 2, operation of mixing system 60 will now be described. Dilution gas flows in the direction of arrow 150 into dilution inlet 66, typically at ambient pressure. Dilution flow continues through flow meter 73. When the dilution gas reaches elbow duct first end 92, the dilution gas will be at a first pressure, typically lower than the dilution inlet pressure due to losses in the system. As the dilution gas flows through elbow duct 90 toward elbow duct second end 94, a pressure differential is formed across the diameter of elbow duct 90. Pressure gain occurs along the elbow duct outer turning radius. By connecting gaseous inlet 100 to elbow duct outer portion 96, this pressure gain is utilized. That is, gaseous inlet 100 is at a second pressure that is greater than the first pressure (at elbow duct first end 92).

Figure 3:
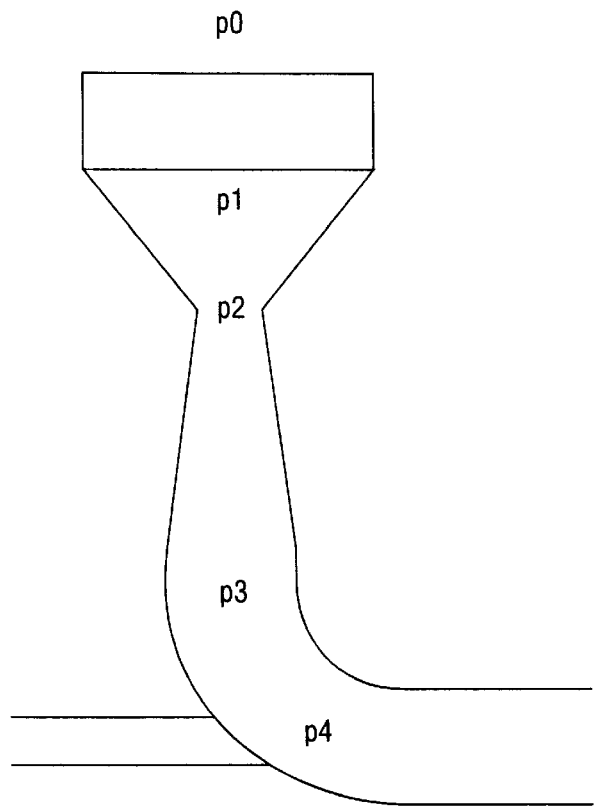
FIG. 3 is a schematic diagram illustrating the pressures at different places in a mixing system of the present invention.

With reference to FIG. 3, a schematic diagram of an illustrative embodiment of the present invention is illustrated. Prior to the inventors testing a prototype, pressure losses were calculated as a function of the physical system parameters, depicted in FIG. 3, as follows:

The filter and heater losses:

$$p_b = p_1 + \Delta p_{filter}$$

wherein $p_b$ is the pressure at the dilution inlet (typically ambient), $p_1$ is the pressure at the flow meter inlet, and $\Delta p_{filter}$ is the total pressure loss of the filter and heater. The losses from a typical filter/heater may depend on flow and may be around 0.5 in $H_2O$ (0.13 kPa) at 1,000 $ft^3/min$ (28.3 $m^3/min$).

For the converging cone, there is the acceleration of the flow and the smooth approach orifice (SAO) entrance cone losses:

$$p_1 = p_2 + \frac{1}{2}\rho\left(\frac{Q}{A_2}\right)^2 + K_{L_e}\frac{1}{2}\rho\left(\frac{Q}{A_2}\right)^2$$

wherein $p_2$ is the flow meter throat pressure, $\rho$ is the fluid density, Q is the flow rate, $A_2$ is the throat cross-sectional area, and $K_{L^e}$ is a loss constant. Typically, the entrance loss factor $K_{L_e}$ is about 0.02; the density of air is 1.2 g/l. For a flow of 500 $ft^3/min$ (14.2 $m^3/min$) and an area $A_2$ for a 3.45 in (88 mm) throat diameter $p_2$ will be about 3.7 in $H_2O$ (0.92 kPa) below atmospheric.

The pressure recovery of the diffuser cone is described by the pressure recovery coefficient $C_p$:

$$p_3 = p_2 + C_p\frac{1}{2}\rho\left(\frac{Q}{A_2}\right)^2$$

wherein $p_3$ is the pressure at the exit cone outlet, and $C_p$ is the pressure recovery coefficient. The value of $C_p$ depends on the area ratio $A_3/A_2$. For an expansion to a 6 in (152 mm) pipe with the cone angles recommended herein, $C_p$ is about 0.80.

Losses from the elbow depend on the radius to diameter ratio. There is also the elbow flow-meter effect, leading to the pressure recovery related to the inside to outside differential pressure, and described by the $X_x$ coefficient, which depends somewhat on flow rate and construction but has a value of about 0.5:

$$p_4 = p_3 - K_{L_{elbow}} \frac{1}{2} \rho \left(\frac{Q}{A_3}\right)^2 + C_x \cdot \rho \cdot \frac{d}{r} \left(\frac{Q}{A_3}\right)^2$$

wherein $p_4$ is the pressure at the elbow duct outlet, $K_{L^{elbow}}$ is a loss constant, $A_3$ is the outlet cross-sectional area, $d_3$ is the outlet diameter, r is the turning radius of the elbow, and d is the elbow diameter. For a gentle elbow with r/d of about 2.5, the $K_{L^{elbow}}$ is about 0.12. With these parameters, $p_4$ will be about 0.9 in $H_2O$ (0.22 kPa) below atmospheric at 500 ft$^3$/min (14 m$^3$/min) flow.

Figure 4:
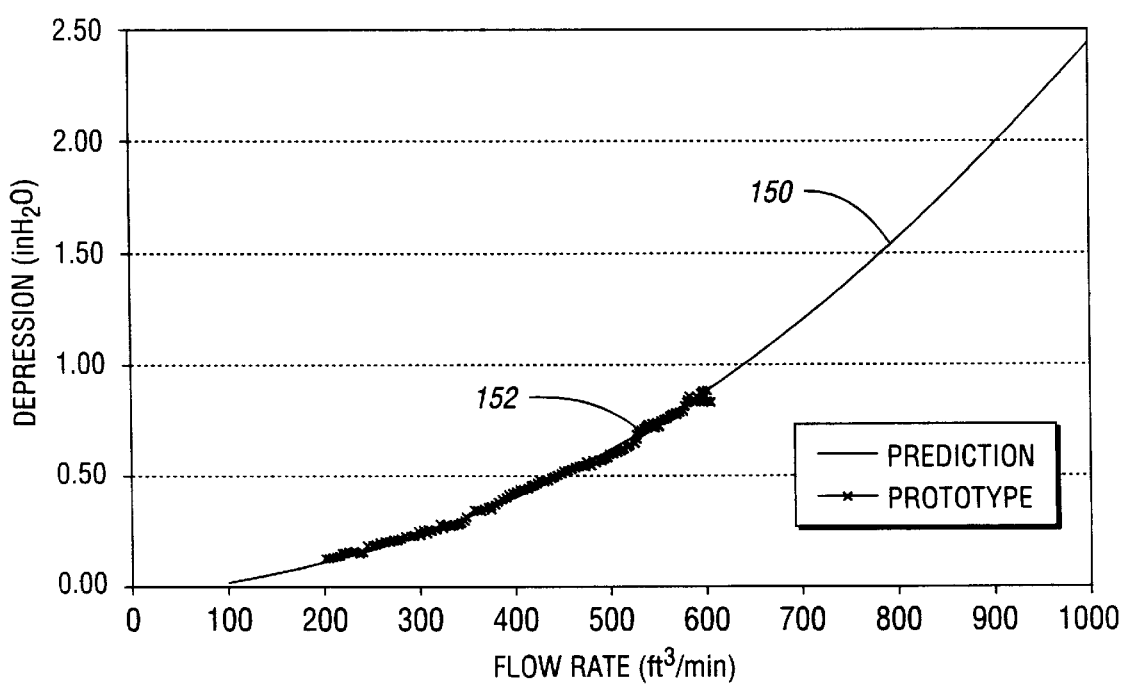
FIG. 4 is a graph depicting gaseous inlet depression in inches $H_2O$ versus flow rate in $ft^3/min$ for a mixing system prototype embodiment made in accordance with the present invention.

With reference now to FIG. 4, a graph depicts a pressure model for a prototype mixing system made by the inventors without a filter or heater. Inlet depression or vacuum is indicated on the ordinate in inches $H_2O$. Flow rate at the mixing system outlet is indicated on the abscissa in ft$^3$/min. Line 150 is the theoretical relationship contemplated by the inventors for the prototype tested. Test points for the prototype are indicated at 152.

Low loss mixing systems of the present invention are capable of meeting the current requirements of automotive exhaust sampling without blowers, moving parts or complicated control systems. Minimal suction or back-pressure to the test vehicle tail pipe is achieved by a unique juxtaposition of the necessary sample elements, including filtering and flow measure devices when required.

Appropriate ordering of components in the flow path is desired for preferred embodiments of the present invention. Bringing dilution air to the point where it mixes with exhaust gas is complicated by the need to filter it and to measure its flow rate. These elements create pressure drops which are expressed as suction on the vehicle tail pipe. By placing these elements in an order that is friendly to the dilution air path, the pressure drops can be minimized. Putting the large filter areas before the flow measuring devices means that it is not necessary to have a loss generating deceleration of the flow before it reaches the mixing zone.

A carefully calculated recovery cone at the exit of a smooth approach orifice (SAO) is desired for preferred embodiments of the present invention. The desire to measure the dilution air flow puts a disturbance in the dilution air path. An SAO is an accurate way to make this measurement. The disturbance to the flow path and the resulting pressure losses are minimized by using a recovery cone in the path from the measuring throat that has a carefully chosen and gentle expansion angle.

A larger radius elbow to turn the air flow without excessive pressure losses is desired for preferred embodiments of the present invention. In a practical component layout, it is usually necessary to turn the air flow so that the components and ducts will fit in a typical test cell. This is done with a large radius elbow so that the flow losses from separation at the inside of the bend are minimized.

An exhaust inlet strategically located on the elbow bend is desired for preferred embodiments of the present invention. Because the flowing air in the dilution air path has mass, it takes a force to turn the flow. Normally the force is provided by the walls of the elbows that re-direct the flow. This phenomenon results in a pressure difference between the inside and outside of the flow. In particular, there is a pressure enhancement on the outside of the bend that can cancel much of the other pressure losses. The location of the exhaust inlet is chosen to take the most advantage of this effect. The relative sizes of the main pipe, inlet pipe and radius of the bend are chosen according to the expected operating range of flows to optimize these effects and minimize the undesirable pressure variations observed at the test vehicle.

It is to be appreciated that many of the design parameters for embodiments of the present invention have relationships with each other that allow design optimization based upon the mixing system application. One of ordinary skill in the art would appreciate that changes to design parameters may be made without departing from the scope of the present invention. For example, for smaller diameter elbow ducts, the pressure differential across the elbow duct is larger at the same flow rate. Further, this higher pressure differential would be required if the pressure losses through the flow meter are large.

Further, depending on the choice for the transducer that monitors the flow meter, a smaller cross-section may be required at the flow meter to provide adequate input for the transducer. The above description of some design parameters in embodiments of the present invention is exemplary only, and is by no means meant to be an exhaustive description.

Further, the elbow duct may turn any number of degrees so long as the gain along the outside portion of the elbow duct is sufficient for the intended application of the mixing system. Still further, embodiments of the present invention may also be used in traditional mixing system applications which do not require a flow meter. In such applications, the gain of an elbow shaped duct may be employed to reduce gaseous inlet depression at higher flow rates, without a flow meter.

Even further, although it is a primary advantage of embodiments of the present invention that the passive gain of the elbow allows for lower cost mixing systems without an active control blower, a blower may be employed, if desired, to provide a pressure gain within the system. For example, extremely aggressive testing procedures may be contemplated in the future which are so demanding that even the passive gain from an elbow shaped duct does not provide the desired amount of vacuum reduction. In such applications, the elbow shaped duct may be employed to provide some passive gain while employing a blower to provide additional pressure gain.

While the best mode for carrying out the invention has been described in detail, those familiar with the art to which this invention relates will recognize various alternative designs and embodiments for practicing the invention as defined by the following claims.

What is claimed is:

1. A mixing system for diluting gases wherein the gases are at approximately ambient pressure and are passively collected to avoid significant disturbances to the pressure of the gases, the mixing system comprising:

a dilution inlet for receiving a dilution gas at approximately the ambient pressure;

an elbow duct having a first end in flow communication with the dilution inlet and a second end outlet for connecting to external equipment, the elbow duct defining an inner turning radius and an outer turning radius; and a gaseous inlet for passively receiving the gases at approximately the ambient pressure, the gaseous inlet being in flow communication with the elbow duct along the elbow duct outer turning radius to reduce depression at the gaseous inlet.

2. The mixing system of claim 1 wherein the elbow duct has an average turning radius to diameter ratio between about 0.5 and about 2.5, and has a bend between about 45 degrees and about 180 degrees.

3. The mixing system of claim 1 further comprising filters at the dilution inlet for filtering the dilution gas.

4. The mixing system of claim 1 further comprising a heater at the dilution inlet for heating the dilution gas.

5. A mixing system for diluting gases, the mixing system comprising:
   a dilution inlet for receiving a dilution gas;
   a flow meter having an inlet in flow communication with the dilution inlet, and having an outlet;
   an elbow duct having a first end in flow communication with the flow meter outlet, and a second end outlet for connecting to external equipment, the elbow duct defining an inner turning radius and an outer turning radius; and
   a gaseous inlet for receiving the gases, the gaseous inlet being in flow communication with the elbow duct along the elbow duct outer turning radius.

6. The mixing system of claim 5 wherein the flow meter inlet defines a narrowing portion, and the flow meter outlet defines an exit cone.

7. The mixing system of claim 6 wherein the exit cone has an exit cone angle between about 5 degrees and about 15 degrees.

8. A mixing system for diluting gases wherein the gases are at approximately ambient pressure and are passively collected to avoid significant disturbances to the pressure of the gases, the mixing system comprising:
   a dilution inlet for receiving a dilution gas at approximately the ambient pressure;
   an elbow duct having a first end in flow communication with the dilution inlet, the elbow duct having a second end outlet, and the elbow duct defining an inner turning radius and an outer turning radius;
   a gaseous inlet for passively receiving the gases at approximately the ambient pressure, the gaseous inlet being in flow communication with the elbow duct along the elbow duct outer turning radius to reduce depression at the gaseous inlet; and
   a sampling system connected to the elbow duct second end outlet.

9. The mixing system of claim 8 wherein the elbow duct has an average turning radius to diameter ratio between about 0.5 and about 2.5, and has a bend between about 45 degrees and about 180 degrees.

10. The mixing system of claim 8 further comprising filters at the dilution inlet for filtering the dilution gas.

11. The mixing system of claim 8 further comprising a heater at the dilution inlet for heating the dilution gas.

12. A mixing system for diluting gases, the mixing system comprising:
    a dilution inlet for receiving a dilution gas;
    a flow meter having an inlet in flow communication with the dilution inlet, and having an outlet;
    an elbow duct having a first end in flow communication with the flow meter outlet, the elbow duct having a second end outlet, and the elbow duct defining an inner turning radius and an outer turning radius;
    a gaseous inlet for receiving the gases, the gaseous inlet being in flow communication with the elbow duct along the elbow duct outer turning radius; and
    a sampling system connected to the elbow duct second end outlet.

13. The mixing system of claim 12 wherein the flow meter inlet defines a narrowing portion, and the flow meter outlet defines an exit cone.

14. The mixing system of claim 13 wherein the exit cone has an exit cone angle between about 5 degrees and about 15 degrees.

15. A mixing system for diluting gases, the mixing system comprising:
    a dilution inlet for receiving a dilution gas;
    a flow meter having an inlet in flow communication with the dilution inlet, and having an outlet;
    a curved elbow duct having a first end in flow communication with the flow meter outlet, a curved outer portion, and a second end outlet for connecting to external equipment, wherein dilution gas at the elbow duct first end is at a first pressure during mixing system operation; and
    a gaseous inlet for receiving the gases, the gaseous inlet being in flow communication with the elbow duct along the outer portion of the elbow duct such that gases at the gaseous inlet are introduced at the elbow duct curved outer portion at a second pressure that is greater than the first pressure during mixing system operation.

16. The mixing system of claim 15 further comprising a heater at the dilution inlet for heating the dilution gas.

17. The mixing system of claim 15 further comprising:
    a sampling system connected to the elbow duct second end outlet.

18. The mixing system of claim 15 wherein the elbow duct has an average turning radius to diameter ratio between about 0.5 and about 2.5, and has a bend between about 45 degrees and about 180 degrees.

19. The mixing system of claim 15 wherein the flow meter inlet defines a narrowing portion, and the flow meter outlet defines an exit cone.

* * * * *